United States Patent [19]

Magnus et al.

[11] Patent Number: 5,220,016
[45] Date of Patent: Jun. 15, 1993

[54] SYNTHESIS OF NAVELBINE ANALOGS

[75] Inventors: Philip D. Magnus, Austin, Tex.; Lee S. Thurston, Worthington, Ohio

[73] Assignee: Board of Regents, The University of Texas System, Austin, Tex.

[21] Appl. No.: 736,300

[22] Filed: Jul. 29, 1991

[51] Int. Cl.[5] .................. C07D 461/00; C07D 227/00; C07B 49/00

[52] U.S. Cl. ...................................... 540/478; 546/51; 546/201

[58] Field of Search ........................................ 540/478

[56] References Cited

U.S. PATENT DOCUMENTS 4,307,100 12/1981 Langlois et al. ...................... 546/51

OTHER PUBLICATIONS

Magnus, J.A.C.S. 112, 8210-8212 (1990).
Marty, Nouv. Rev. Fr. Hematol 31, 77 (1989).
Fumoleau, Proc. Asco 9, 21 (1990).
Berthaud Proc. Asco 9, 237 (1990).
Kutney, et al., Abstract of U.S. Pat. No. 5,047,528, "Process of Synthesis of Vinblastine and Vincristine," Official Gazette 446-447 (Sep. 10, 1991).
Guéritte et al., "Composés Antitumoraux du Groupe dérivés la vinblastine: dé de la nor -5' Anhydrovinblastine," Eur. J. Med. Chem. Chim. Ther., 18:419-424 (1983).
Potier, "The Synthesis of Navelbine ® Prototype of a New Series of Vinblastine Derivatives," Seminars in Oncology 16 (2, sup. 4):2-4 (Apr. 1989).
Kutney et al., "Studies on the Synthesis of Dimeric Vinca Alkaloids," J. Am. Chem. Soc., 90:4504-4505 (1968).
Mangeney et al., "A New Class of Antitumor Compounds: 5'-Nor and 5',6'-Seco Derivatives of Vinblastine-Type Alkaloids," J. Org. Chem. 44(22):3765-3768 ((1979).
Maral et al., "Experimental in vivo Cross-resistance of Vinca Alkaloid Drugs," Cancer Chemother. Pharmacol., 5:197-199 (1981).
Magnus, et al., "Synthesis of the Vinblastine-like Antitumor Bis-Indole Alkaloid Navelbine Analogue Desethyldihydronavelbine," J. Org. Chem. 56:1166-1170 (1991).
Büchi et al., "Voacamine and Voacorine," J. Am. Chem. Soc., 86:4631-4641 (1964).
Binet et al., "Immunofluorescence Study of the Action of Navelbine, Vincristine and Vinblastine on Mitotic and Axonal Microtubules," Int. J. Cancer 46:262-266 (1990).
Bettoni et al., "Absolute Configuration and Optical Purity or 3-Substituted Piperidines," Gazzetta Chimica Italiana 102:189-195 (1972).
Akkerman et al., "Synthetic Oxytocics. I. 3-(-Piperidyl-(N)-Methyl-)Indoles and Related Compounds," Recueil 70:899-916 (1951).
A. Fellous, et al., "Biochemical Effects of Navelbine ® on Tubulin and Associated Proteins," Seminars in Oncology, vol. 16(2):9-14 (1989).

Primary Examiner—Mark L. Berch
Attorney, Agent, or Firm—Arnold, White & Durkee

[57] ABSTRACT

The invention is a de novo synthesis of the norcatharanthine moiety of navelbine. The synthesis includes condensing a Grignard reagent prepared from an amine-protected R(+)-piperidinyl methanol with an N-protected 2-methoxyoxalyl indole. The indole N-protecting group is removed to provide a 2-methoxyindole hydroxy ester which is coupled to vindoline. After removal of the amineprotecting group from the piperidinyl group, ring closure to the indole moiety provides dihydrodesethyl navelbine. Other derivatives and analogs of navelbine with potential clinical applications in cancer chemotherapy may be readily synthesized. The synthesis opens a route to a wide variety of navelbine modifications, including modifications at or near the tryptamine bridge.

9 Claims, 2 Drawing Sheets

SYNTHESIS OF NAVELBINE ANALOGS

The United States Government may have certain rights in the present invention pursuant to the terms of National Institutes of Health Grant No. GM29081.

BACKGROUND OF THE INVENTION

1. Field of the Invention

The invention relates to the preparation of navelbine and novel analogs and derivatives of navelbine through a de novo synthesis of the nor-catharanthine moiety of the bis-indole vinblastine. Anti-tubulin activity of a navelbine derivative prepared by the novel synthesis is disclosed.

2. Description of Related Art

The synthesis of Vinca plant alkaloids and related compounds is of interest because of the anti-tumor activity of many of these compounds. Vinblastine is the archetype of a class of dimeric alkaloids well-known for the ability to disrupt microtubule formation, the property apparently crucial to its anti-tumor activity. Vinblastine and related compounds have been used for treatment of Hodgkin's disease and ovarian cancer (Lhomme, 1990).

Unfortunately, as with many drugs, in vivo cross resistance of vinca alkaloid drugs often arises (Maral, et al., 1981). Another disadvantage of these drugs is their toxicity, particularly neurotoxicity (Binet et al., 1990). This has stimulated efforts to synthesize analogs of the vinca alkaloids that retain antimitotic activity while showing reduced toxicity.

Total synthesis of vinblastine has not been achieved; however, various non-naturally occurring Vinca alkaloid compounds have been prepared, the most significant of which is navelbine, the nor-anhydro analog of vinblastine. Navelbine is of interest because it has exhibited broader antitumor activity and lower neurotoxicity and other side effects than vinblastine and vincristine (Fellous et al., 1989).

Navelbine has not previously been totally synthesized. Its preparation has been based a two-step reaction from anhydrovinblastine involving N-oxide formation, followed by a Polonovski rearrangement. Two significant disadvantages of this preparation are the inefficiency of the synthesis (Gueritte et al., 1983) and that the preparation of derivatives is limited to reactions that can be run on either the starting bis-alkaloid (vinblastine) or its nor-analog, navelbine.

Consequently, few derivatives of navelbine have been prepared. While relatively simple compounds such as desacetylnavelbine are known, most navelbine-related compounds are limited to straightforward functionalizations across the 5-'4' double bond of navelbine (Langlois et al., 1981). Some of these compounds have varying degrees of antileukemic activity, although none appear significantly superior to the parent compound. There is significant interest and perceived need in developing routes to a wide range of navelbine analogs and related compounds for testing in cancer chemotherapy.

SUMMARY OF THE INVENTION

The present invention addresses one or more of the problems encountered in the synthesis of new vinblastine-related analogs. A de novo synthesis of the nor-catharanthine moiety of navelbine is disclosed which allows access to a wide variety of navelbine analogs not previously available. Several analogs and derivatives are likely to be useful as clinically active agents.

The method is a process for the preparation of navelbine by way of a partial total synthesis of one of the dimeric components. The synthesis includes condensing a Grignard reagent prepared from an amine-protected R(+)-piperidinyl methanol with N-protected 2-methoxyoxalyl indole. After condensation, the indole N-protecting group is removed to give a 2-methoxyindole hydroxyester which is then coupled to vindoline. The piperidinyl amine-protecting group is removed. Navelbine results from ring closure between the piperidinyl nitrogen and the indole moiety.

Overall the method provides a novel synthesis or process for the preparation of navelbine, navelbine derivatives or navelbine analogs. Navelbine is similar in structure to the well-known anti-tumor compound vinblastine. It differs from vinblastine in having one less carbon moiety between the tryptamine bridge and the indole moiety. Navelbine is of particular interest because of its anti-tumor properties and its decreased cytotoxicity compared with Vinblastine. New navelbine derivatives or analogs may now be synthesized which have previously been difficult or impossible to obtain from reactions on intact navelbine.

A preferred starting material for the synthesis of Navelbine is a nipecoic acid ester which is preferably the levorotatory ester in order to provide ultimately the correct stereochemistry of navelbine. Typically, the ester will be a simple methyl or ethyl ester although in theory any of a number of lower alkyl groups (1-5 carbon atoms) could be used or, alternately, the free acid, provided that during the reduction step the ester is converted to a primary alcohol. Although typically the group alpha to the ester group of nipecoic acid is hydrogen, other groups may be present resulting in a substitution at the 2-position of navelbine. An alkyl ester of nipecoic acid may be conveniently reduced by treatment, for example, with lithium aluminum hydride in tetrahydrofuran at reflux. Other reducing agents could be used, for example, lithium borohydride.

For the purpose of synthesizing a navelbine analog with a bridge between the indole and the tryptamine nitrogen, a protecting group is attached to the nipecoic acid nitrogen group. Ideally this group is compatible with subsequent transformations and readily removed under mild conditions. Several groups are suitable, including a N-carboxybenzoyloxy group, N-benzoyl group or N-benzyl group. In preferred practice, an N-allyl protecting group is used which is readily attached by appropriate reaction with allyl bromide.

The primary alcohol produced from the reduction of an alkyl ester of nipecoic acid may then be reacted with, for example, mesyl chloride in triethylamine and dichloromethane, followed by reduction with a reducing agent such as lithium bromide in acetone with magnesium at reflux to provide a Grignard reagent from the primary alcohol.

The Grignard reagent prepared from alkyl nipecotate is next condensed with a protected methoxyoxalyl indole. The indole nitrogen is preferably protected with a group such as N-phenylsulfonyl. Condensation with the Grignard reagent will occur alpha to the indole nitrogen to form an N-phenylsulfonyl alpha hydroxy ester. The indole nitrogen protecting group is readily cleaved from the condensation product to produce an N-allyl alpha hydroxy ester of methoxyoxalyl indole. This product is generally a mixture of stereoisomers but separation is unnecessary since subsequent coupling with vindoline yields a one-to-one mixture at the stereogenic center. Removal of the protecting phenylsulfhydryl group is readily accomplished; for example, by treatment with 1-chloroethyl chloroformate followed by heating the intermediate carbamate in methanol at reflux to give the secondary amine.

A dimeric compound which is the direct precursor of navelbine is prepared by coupling the alpha hydroxy ester compound with vindoline. This may be accomplished by heating the two compounds in a mixture of hydrochloric acid and methanol at reflux for a period of time up to two hours. This results in a one-to-one diastereomeric mixture at the 18' position of navelbine. Such diastereomers may be separated by preparative high performance liquid chromatography (HPLC) or other methods well known to those of skill in the art. The nipecoic acid ester protecting group may be removed as appropriate to the nature of the protecting group. In a preferred embodiment, an allyl protecting may be removed by heating with 1-chloroethyl chloroformate in methanol, restoring the secondary amine.

In a final step, navelbine and/or its analogs may be formed by ring-closing the deprotected amine from the dimeric compound. This is conveniently done with an intramolecular Mannich type reaction which forms the 8-member ring of navelbine. In a typical procedure the secondary amine may be heated at slightly elevated temperature, about 40° C., in aqueous formaldehyde and glacial acetic acid. The product is desethyldihydro navelbine.

Novel compounds related to navelbine may be synthesized by modifications at many points in the de novo synthesis. For example, in the condensation reaction to form the dimeric alkaloid, vindoline need not be the condensing moiety. Other groups such as aryl groups or substituted aryl groups, could be coupled in place of vindoline. Variations in the ring size may be made by modifying the starting material related to nipecoic acid. Seven or 8-membered rings for example could be used in place of nipecoic acid. Other potential modifications include the use of 2-ethoxy or other alkoxyoxalyl indoles in the first condensation step.

Another aspect of the invention is the synthesis of derivatives at the carbon linkage between the tryptamine nitrogen and the C-9 position on the indole ring. Exemplary substituents include lower alkyls from 1-5 carbon atoms, carboxyl, alkanols, alkylamines and alkyl thiols. Alternatively, heteroatoms could be inserted between the tryptamine nitrogen and carbon-9 of the indole moiety.

In still further embodiments of the invention, various substitutions may be made at the carbon between the tryptamine bridge and the $C_{18}$ of the indole ring, for example, spirocyclic systems with the spiro carbon between the tryptamine bridge nitrogen and the 9-carbon of the indole.

DETAILED DESCRIPTION OF PREFERRED EMBODIMENTS

Materials and Methods

Tetrahydrofuran was freshly distilled from sodium benzophenone ketyl under argon. All other chemicals were reagent grade or better.

Infrared spectra were obtained from solution in chloroform or neat using a Perkin Elmer 1600 FTIR. Ultraviolet spectra were obtained from solution in methanol using a Lambda 3B UV/vis spectrophotometer. $^1$H NMR and $^{13}$C NMR were recorded using a GE 300 instrument at 300 and 75 MHz respectively.

Circular dichroism spectra were recorded on a Jasco J-20A recording spectropolarimeter for solutions in MeOH and reported as $\lambda_{max}$ and $\Theta$ (differential absorptivity). $[\phi]=[\Psi]M/100=3300\Delta\epsilon$ where $[\Theta]=$molecular ellipticity, $[\Psi]=$specific ellipticity and M=molecular weight.

Optical rotations were recorded using a 10 cm, 1 ml cell on a Perkin Elmer 241 MC Polarimeter.

Thin layer chromatography was performed on Merck silica gel 60 F-254 (nm) analytical plates.

Flash chromatography was conducted using Merck silica gel 60 (230-400 mesh).

Preparative HPLC was performed on a Rainin Dynamza $SiO_2$ column with a 11 cm guard column, eluting with 81:15:4 ethyl acetate/dichloromethane/methanol (containing 10% $NH_4OH$) at 40 ml/min, 300 psi.

Melting points were obtained on a Thomas-Hoover capillary melting point apparatus and are uncorrected.

The following examples illustrate preferred embodiments of the practice of the invention. It should be understood that these examples are intended to be illustrative of the invention and in no way limiting unless otherwise specified in the claims.

The following examples are intended to be illustrative and it is understood that the invention disclosed herein suitably may be practiced in the absence of any element which is not specifically disclosed herein.

EXAMPLE 1

Total Synthesis of Desethyldihydro Navelbine

Figure 1:
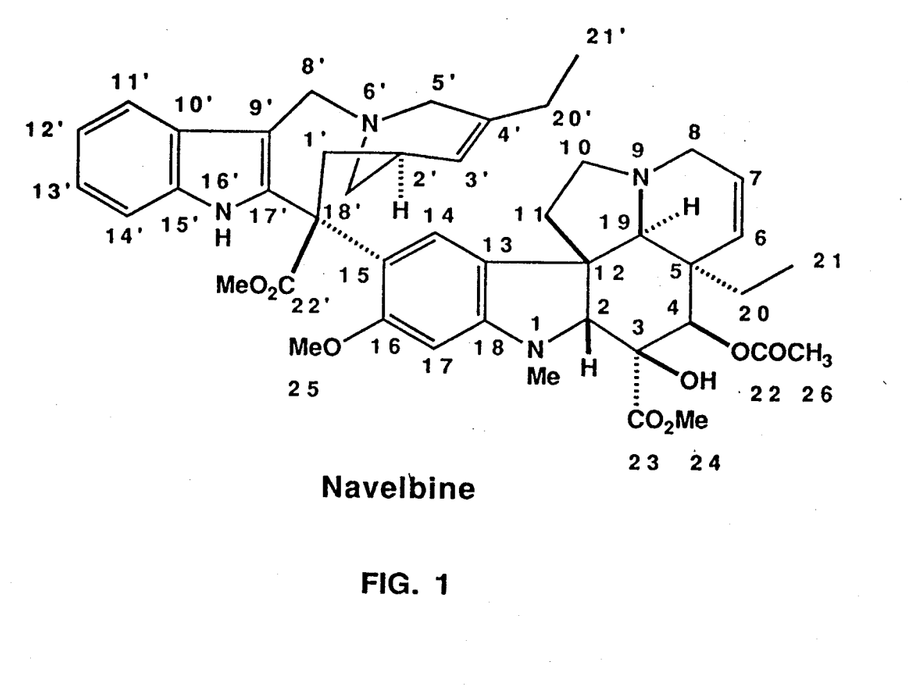
FIG. 1 shows the structure of navelbine.
Figure 2:
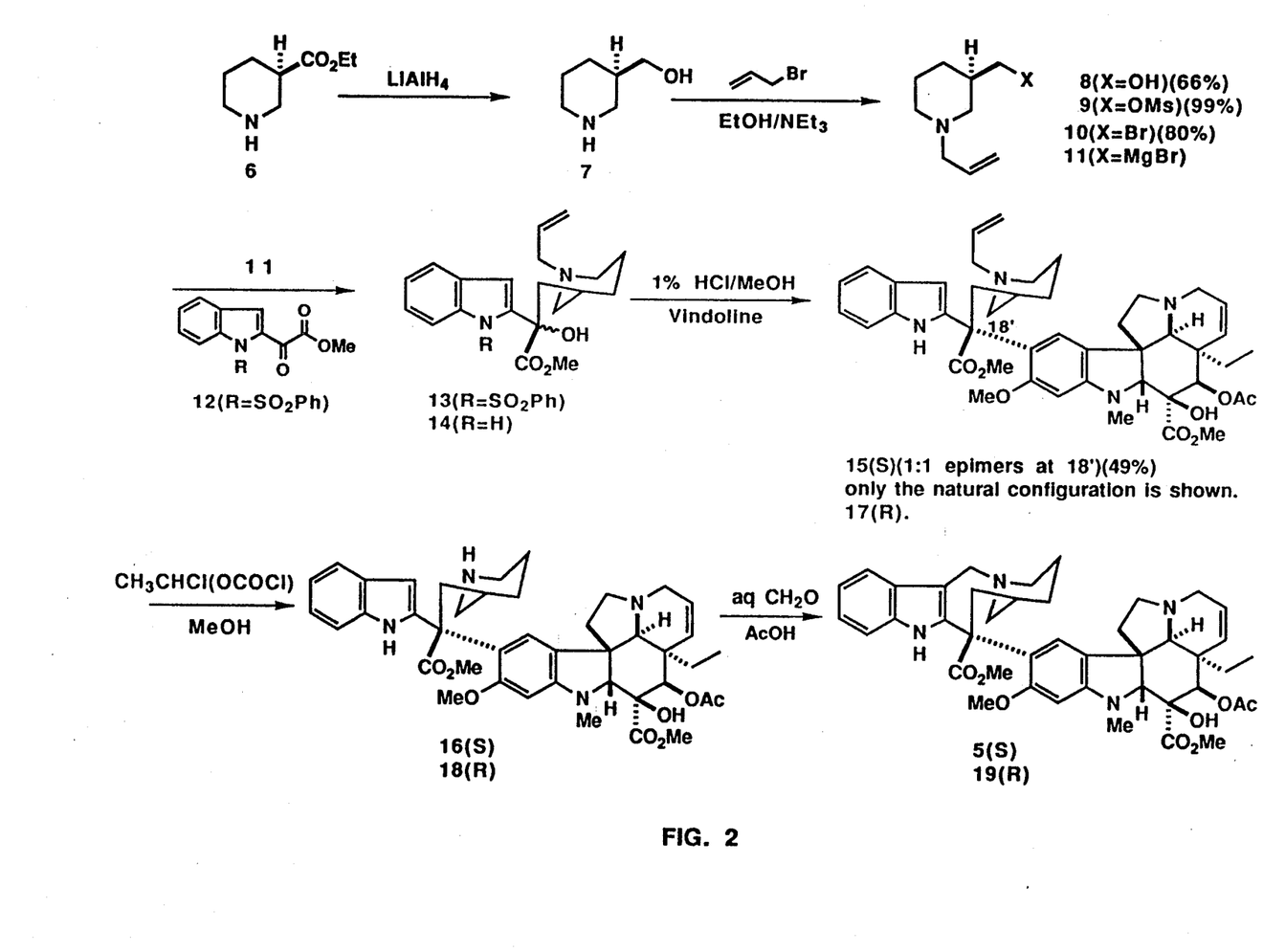
FIG. 2 is a schematic representation of the synthesis of navelbine.

The synthetic route is shown in FIG. 2. Numbers corresponding to the structures in the figure correspond to the compounds in the following synthetic steps.

($\pm$)-Ethyl nipecotate was resolved using L-(+)-tartaric acid and the (+)-tartrate salt was recrystallized from 95% ethanol to give R-(−)-ethyl nipecotate 6 (after liberation of the free base with aqueous sodium hydroxide). Treatment of the nipecotate ester 6 with (+)-α-1-naphthyl ethyl isocyanate gave the derived urea, whose diastereomeric purity ($^1$H NMR) indicated that the nipecotate ester 6 was at least 90% enantiomerically pure. Reduction of the ester by treatment with $LiAlH_4$/THF at reflux for 1 h. gave S-(+)-3-piperidine methanol 7 (89%). After examining the N-carbobenzyloxy, N-benzyl and N-allyl groups as potential amine protecting groups, the N-allyl group was found to be most compatible with subsequent transformations and readily removed under mild conditions. Treatment of the primary alcohol 7 with allyl bromide in ethanol containing triethylamine, heated TM at reflux, gave the N-allyl amine, 8 (66%). Mesylation of the amine 8 ($MsCl/Et_3N/CH_2Cl_2$) gave the mesylated compound 9 (99%), which was directly converted into the bromide 10 (80%) by treatment with lithium bromide in acetone at reflux.

N-Phenylsulfonyl-2-methoxyoxalyl indole 12 was treated with the Grignard reagent 11 at 0° C. to give the α-hydroxy ester 13 (68%) as a mixture of diastereomers (1:1). In was not necessary to separate these diastereomers since the coupling reaction with vindoline gives a 1:1 mixture at the stereogenic center. Reductive cleavage of the phenylsulfonyl group from the indole nitrogen atom to give the N-allyl-α-hydroxy ester 14 was accomplished in 88% yield by treatment of α-hydroxy ester 13 with sodium naphthalenide in dimethoxyethane at −50° C., followed by quenching with trifluoroacetic acid. Coupling of the N-allyl-α-hydroxy ester 14 with vindoline was achieved using conditions analogous to those used in the synthesis of the bis-indole alkaloid dihydrovincamine (Büchi et al., 1964). The N-allyl-α-hydroxyester 14 in 1% HCl/MeOH containing 1.1 equivalents of vindoline was heated at reflux for 2 hr to give the dimer 15 (49%) as a 1:1 diastereomeric mixture at 18′. The diastereomers were separated by preparative HPLC and the assignment of absolute configuration at 18′ could be made from the comparison of the CD spectra with vinblastine and navelbine.

The allyl protecting group was removed by treatment of the dimer 15 with 1-chloro-ethyl chloroformate followed by heating the intermediate carbamate in methanol at reflux to give the secondary amine 16 (74%). An intramolecular Mannich reaction served to form the eight-membered ring of navelbine. A solution of the secondary amine 16 in aqueous formaldehyde and glacial acetic acid was heated at 40° C. for 24 hr to provide desethyldihydro-navelbine 5 (81%). The CD spectrum of desethyldihydro navelbine 5 was very similar to navelbine and the $^1$H NMR spectrum exhibited an AB quartet for the newly introduced methylene hydrogens at δ 4.70(J=13Hz) and 4.47 (partly resolved) very similar to navelbine itself. Carrying out the same series of transformations on the 18′-epimer, namely compound 17, the 18′(R)-epimer 19 was obtained via compound 17.

The natural 18′(S)-epimer 5 exhibited in vitro antitumor activity comparable to vinblastine, whereas the 18′(R)-epimer 19 was inactive (see Example 4).

Resolution of R-(−)-Ethyl Nipecotate 6

(±)-Ethyl nipecotate (70.16 g, 71ml) and (+)-tartaric acid (67 g) were dissolved in hot 95% ethanol (350 ml). The resulting solution was allowed to slowly cool to room temperature and refrigerated overnight. The crystals were filtered, washed with cold ethanol, and recrystallized from 95% ethanol (550 ml), cooling as before to give the (+)-tartrate salt of (+)-ethyl nipecotate (42.9 g). M.p. 155–156° C.

$[α]_D^{21}=+52.4°$ (c=2.0 in 0.2% aqueous ammonium molybdate) ($[α]_D^{21}=+51.0°$, Akkerman, et al., 1951). The salt (25 g) was dissolved in water (400 ml), cooled on ice, and 3 N sodium hydroxide was slowly added until the pH reached 11–12. The solution was extracted with chloroform (3×100 ml), dried (Na$_2$SO$_4$) and evaporated in vacuo to give in nipecoate 6 (9.48 g) as a mobile oil. $[α]_D-1.4°$ (c=5.0 in water) ($[α]_D^{21}=+1.8°$, Akkerman, et al., 1951). The enantiomeric purity of the nipecoate 6 was determined to be at least 90% by treatment of 6 with S-(+)-ethyl naphthylisocyanate to give the urea derivative 6a, m.p. 242.5–243.5° C. (M®OH-/Et$_2$O). $^1$H NMR δ 8.15 (1H, d, J=8.3 Hz), 7.81 (2H, m), 7.50 (4H, m), 5.8 (1H, bs), 5.6 (1H, b), 4.04 (2H, m), 3.87 (1H, dd, J=12 and 2 Hz), 3.51 (1H, dt, J=14 Hz), 3.13 (2H, m), 2.50 (1H, m), 1.97 (1H, m), 1.65 (3H, d, J=4 Hz), 1.16 (3H, t, J=4 Hz), the other diastereomer gives 1.28 (eH, t, J=4 Hz). HRMS calcd for C$_{21}$H$_{26}$N$_2$O$_3$. 354.1943. Found 354.1948.

Synthesis of R-(+)-Piperidinomethanol 7

Reduction of (−)-ethyl nipecotate (14.1 g, 0.089 mol) with LiAIH$_4$ (3.54 g, 0.093 mol) in THF (200 ml), using the usual protocols associated with this reagent gave the piperidinomethanol 7 (9.1 g, 0.079 mol, 89%), as a pale yellow oil. $[α]_D^{21}=+3.8°$ (c=18 in pyridine), $[α]_D^{21}=+5.8°$, Bettoni et al., 1972). $^1$H NMR (CDCl$_3$) δ3.50–3.31(4H, m), 3.15 (1H, d, J=12.0 Hz), 2.98 (1H, d, J=12 Hz), 2.53 (1H, dt, J's=11.74 and 2.82 Hz), 2.32 (1H, m), 1.81–1.60 (3H, m), 1.47 (1H, m), 1.11 (1H, m). This material was used directly in the next step.

Synthesis of R-(+)-N-Allyl-3-Piperidinomethanol 8

To a solution of the piperidinomethanol 7 (0.23 g, 2 mmol) in ethanol (5 ml) and triethylamine (2.8 ml, 10 equiv) was added allyl bromide (0.35 ml, 2.0 equiv) and the mixture heated at reflux for 12 hr. The mixture was evaporated in vacuo and the residue dissolved in chloroform and washed with 5% aqueous K$_2$CO$_3$ (5×10ml). The chloroform layer was dried (MgSO$_4$) and evaporated in vacuo to give the N-allyl derivative 8 (0.20 g, 66%). $[α]_D^{23}=+19.0°$ (c=5 in absolute ethanol). $^1$H NMR (CDCl$_3$) δ5.89 (1H, m), 5.15 (2H, m), 3.57 (1H, dd, J's=10.64 and 4.77 Hz), 3.44 (1H, dd, J's=10.71 and 6.21 Hz), 3.38 (1H, bs), 2.98 (2H, d, J=6.55 Hz), 2.83 (1H, d, J=8.68 Hz), 2.75 (1H, m), 2.02 (1H, m), 1.85–1.57 (5H, m), 1.04 (1H, m). $^{13}$C NMR (CDCl$_3$) δ134.5, 117.8, 65.5, 62.0, 57.0, 53,9, 38,4, 27.1, 24.5. HRMS calcd for C$_9$H$_{17}$NO 155.1310. Found m/e 155.1295.

Synthesis of R-(+)-N-Allyl-3-Piperidinomethanol Methanesulfonate 9

The alcohol 8 (1.3 g, 8.38 mmol) was converted into its methanesulfonate ester 9 (1.96 g, 99%), in the standard manner. $[α]_D^{23}=+10.02°$ (c=5 in absolute ethanol). IR (CHCl$_3$) 2931, 1466, 1334, 1172, 1043, 955 and 820 cm$^{-1}$. $^1$H NMR (CDCl$_3$) δ5.84 (1H, m), 5.16 (2H, m), 4.11 (2H, m), 3.01 (3H, s), 2.98 (2H, d, J =8.1 Hz), 2.87 (1H, m), 2.77 (1H, m), 2.09–1.97 (2H, m), 1.86 (1H, t, J=10.3 Hz), 1.77–1.58 (3H, m), 1.10 (1H, m). $^{13}$C NMR (CDCl$_3$) δ134.77, 118.03, 72.27, 62.00, 55.91, 53.75, 37.79, 26.49, 24.17. HRMS Calcd for C$_{10}$H$_{19}$NO$_3$S233.1086. Found m/e 33.1075.

Synthesis of R-(+)-N-Allyl-3-Piperidinomethyl Bromide 10

To a solution of methanesulfonate ester 9 (9.6 g, 0.04 mol) in acetone (100 ml) was added lithium bromide (6.9 g, 0.08 mol) and the suspension heated at reflux for 18 hr. The acetone was evaporated in vacuo, and the residue partitioned between chloroform and cold aqueous 5% K$_2$CO$_3$ solution. The chloroform layer was dried (MgSO$_4$), filtered, and evaporated in vacuo to give a brown oil. Fractional distillation gave the piperidinomethyl bromide 10 (6.97 g, 80%), b.p. 110° C./0.1 mm. $[α]_D^{23}=+22.3°$ (c=10 in chloroform). IR (thin film) 2932, 2789, 1640, 1465, 1451, 1437, 1340, 1295, 1137, 1084, 995 and 918 cm$^{-1}$ $^1$H NMR (CDCl$_3$) δ5.86 (1H, m), 5.17 (2H, m), 3.30 (2H, m), 3.02 (2H, d, J=6.5 Hz), 2.98 (1H, m), 2.80 (1H, dd, J's=7.6 and 3.4 Hz), 1.97 (2H, m), 1.82 (2H, d, J=10.8 Hz), 1.65 (2H, m), 1.08 (1H, dt, J's=12.5 and 4.5 Hz). $^{13}$C NMR (CDCl$_3$) δ

135.0, 117.4, 61.8, 58.0, 53.6, 38.2, 36.9, 29.3, 24.4. Anal. calcd for $C_9H_{16}NBr$ C, 49.56; H, 7.39; N, 6.42. Found C, 49.32; H, 7.43; N, 6.35.

Synthesis of N-Phenylsulfonyl-2-Methoxalyl Indole 12

To a solution of N-phenylsulfonyl indole (5.14 g, 20 mmol) in dry THF (100 ml) under argon, and cooled to −65° C., was added t-butyl lithium (13 ml, 22 mmol, 1.7 M in pentane). The solution was allowed to warm to 0° C. and stirred for 1 hr. The above solution was added via canula to a stirred solution of dimethyloxalate (9.5 g, 80 mmol) in THF (250 ml) at 0° C. After 4 hrs at 0° C. the mixture was quenched with saturated aqueous $NH_4Cl$ and extracted with ethyl acetate (3×100 ml). The dried ($MgSO_4$) extract was evaporated in vacuo, and the residue purified by chromatography over silica gel eluting with hexane/ethyl acetate (b 10:1) to give the α-keto ester 12 (2.3 g, 34%). M.p. 111–112° C. (from ethyl acetate). IR ($CHCl_3$) 3680, 3619, 3415, 3019, 1743, 1692, 1600, 1537 and 1372 cm$^{-1}$. λmax (ε) (MeOH) 208 (23930), 265 (4460), 275 (4170), 312 (10040) nm. $^1$H NMR ($CDCl_3$) δ8.06 (1H, d, J=8.5 Hz), 7.78 (2H, d, J=7.5 Hz), 7.58 (1H,d, J=8 Hz), 7.51-7.37 (5H, m), 7.29 (1H, t, J=7.6 Hz), 3.99 (3H, s). $^{13}$C NMR ($CDCl_3$) δ177.2, 161.3, 138.5, 136.7, 135.8, 134.1, 129.0, 128.7, 128.5, 127.0, 124.8, 123.4, 122.2, 115.3, 53.3. Anal. calcd for $C_{17}H_{13}NO_5S$ C, 59.47; H, 3.82; N, 4.08. Found C, 59.42; H3.84; N, 3.99%.

Synthesis of Methyl 2-[2-(N-phenylsulfonyl)indolyl]-2-hydroxy-3-[3-(N-allyl piperidine)]propionate 13

To the piperidinomethyl bromide 10 (0.82 g, 3.75 mmol) in a flame dried flask under argon was added Mg powder (0.10 g, 4.125 mmol, 50 mesh) and dry THF (10 ml). The mixture was heated at reflux and two drops of 1,2-dibromoethane added to initiate Grignard reagent formation. After 3 hrs the turbid suspension was cooled to room temperature and added to a solution of the α-keto ester 12 (1.03 g, 3 mmol) in THF (30 ml), at 0° C. under argon. After 30 min the orange solution was quenched with saturated aqueous $NH_4Cl$ solution, and diluted with ethyl acetate (50 ml). The dried ($MgSO_4$) extract was evaporated in vacuo to give the α-hydroxy ester 13 as an orange oil (1.28 g, 68%) consisting of a mixture of diastereomers at C-2 (1:1). For the purpose of characterization, one of the diastereomers was purified by chromatography over silica gel eluting with hexane/ethyl acetate/10% aqueous NH4OH/MeOH (15:3:1) to give the α-hydroxy ester 13 (unknown C-2 configuration). M.p. 186-187.5° C. (from diethyl ether). $[\alpha]_D^{23}$=−12.5° (c=4.4 in $CHCl_3$). IR ($CHCl_3$) 3413, 3013, 2943, 1741, 1653, 1447, 1371, 1202 and 1072 cm$^{-1}$. δmax(ε) (MeOH) 213 (28370), 251 (14700), 339 (1520) nm. $^1$H NMR ($CDCl_3$) δ7.84 (2H, d, J=7.4 Hz), 7.48 (2H, m), 7.40 (2H, m), 7.22 (2H, m), 6.90 (1H, d, J=5 Hz), 5.88 (1H, m), 5.14 (2H, m), 3.78 (3H, s), 3.02- $C_{26}H_{30}N_2O_5S$ 482.1875. Found m/e 482.1863.

Methyl 2-(2-indolyl)-2-hydroxy-3-[3-(N-allylpiperidine)]propionate 14

To a solution of the α-hydroxy ester 13 (a mixture of diastereomers at C-2) (0.265 g, 0.55 mmol) in dry dimethoxyethane (5 ml) at −50° C. under argon was added sodium naphthalenide (1 M soln in THF) until the solution remained pale green. The mixture was quenched with trifluoroacetic acid (0.1 ml), and extracted with ethyl acetate (3×10 ml). The extract was washed with saturated aqueous $NaHCO_3$ solution, dried ($MgSO_4$) and evaporated in vacuo to give the propionate 14 (0.165 g, 88%). The mixture of diastereomers was not separated but chromatagraphed over silica gel eluting with hexane/ethyl acetate/10% aqueous $NH_4OH$/MeOH (5:1:1) to remove more polar impurities. The purified mixture had $[\alpha]_D^{23}$=+7.6° (c=9 in $CHCl_3$). HRMS calcd for $C_{20}H_{26}N_2O_3$ 3422.1943. Found m/e 342.1942. This material was used directly in the next stage (+)-18'S-4'-Desethyl-4'-4'-deshydroxy-6'-allyl-7',8'-bis-norvinblastine 15

A solution of the propionate 14 (0.468 g, 1.36 mmol, mixture of diastereomers) and vindoline (0.686 g, 1.50 mmol, 1.1 equiv) in 1% HCl/MeOH (50 ml) was heated at reflux for 2 hr. The solution was evaporated in vacuo and the residue dissolved in chloroform and washed with saturated aqueous $NaHCO_3$ solution. The chloroform layer was dried over $MgSO_4$, filtered, and evaporated to give a foam consisting of a mixture of 18'S-15 and 18'R-17 (ca.1:1, 0.524 g, 49%). The diastereomeric mixture was separated by preparative HPLC eluting with hexane/$CH_2Cl_2$/MeOH/10% aqueous $NH_4OH$ to give 18'S-15, rf (tlc, silica gel) 0.38 (5:5:1 hexane/EtOAc/MeOH,10% $HN_4OH$). tr (HPLC) 43 min. (81:15:4 the above solvent system). M.p. 155–157° C. $[\alpha]_D^{23}$=+24.8° (c=1.65 in $CHCl_3$). CD (MeOH) λmax (Δε) 210 (−66.3), 222 (+43.2), 256 (+19.5), 305 (+3.1), 312 (+2.8). IR ($CHCl_3$) 3452, 2936, 1740, 1611, 1502, 1456, 1435, 1373, 1235 and 1041 cm$^{-1}$. UV (MeOH) λmax (ε) 213 (48300), 264 (16800), 308 (5940) nm. $^1$H NMR ($CDCl_3$) δ9.65 (1H, bs, NH), 8.90 (1H, bs, OH), 7.49 (1H, d, J=7.6 Hz), 7.20 (1H, d, J=7.8 Hz), 7.06 (2H, m), 6.51 (1H, s), 6.29 (1H, s), 6.03 (1H, s), 5.84 (2H, m), 5.40 (1H, s), 5.27 (1H, d, J=10.3 Hz), 5.13 (2H, m), 3.77 (3H,s), 3.71 (3H, s), 3.67 (3H, s), 3.34 (2H, m), 2.95 (2H, d, J=6.3 Hz), 2.69 (3H, s), 2.56 (1H,s), 2.41 (1H, m), 2.26 (2H, m), 2.08 (3H, s), 2.05-1.63 (5H, m), 1.41 (1H, m), 1.24 (4H, m), 1.24 (4H, m), 0.86-0.72 (2H, m), 0.56 (3H, t, J=7.2 Hz). $^{13}$C NMR ($CDCl_3$) δ175.16, 171.54, 170.73, 158.33, 152.57, 138.89, 135.72, 130.11, 127.73, 124.29, 123.12, 122.14, 121.84, 121.45, 120.17, 119.27, 110.81, 102.44, 93.63, 83.08, 79.73, 76.37, 65.46, 62.14, 55,71, 53.80, 53.15, 52.83, 52.24, 52.12, 50.56, 50.56, 50.44, 44.42, 42.60, 38.25, 32.49, 31.97, 30.59, 21.06, 7.90, and four 3° carbons too weak. HRMS (FAB). Calcd for $C_{45}H_{57}N_4O_8(M^++1)$, 781.4176. Found m/e 781.4235.

18'R-17, r$_f$(tlc, silica gel) 0.5, t$_r$(HPLC) 49 min. M.p. 173–174°. $[\alpha]_D^{23}$=−8.56° (c=1.8 in $CHCl_3$). CD (MeOH) λmax (Δε) 210 (+61.7), 222 (69.9), 269 (+11.3), 305 (−2.6), 312 (−2.6). IR ($CHCl_3$) 3436, 3001, 2931, 1739, 1616, 1502, 1454, 1434, 1372, 1243 and 1041 cm$^{-1}$. $^1$H NMR ($CDCl_3$δ9.71 (1H, s), 7.47 (1H, d, J=7.66 Hz), 7.31 (1H, d, J=8.0 Hz), 7.13-7.00 (2H, m), 6.70 (1H, s), 6.16 (1H, s), 6.01 (1H, s), 5.85 (1H, dd, J's=10.0 and 3.77 Hz), 5.63 (1H, m), 5.40 (1H, s), 5.24 (1H, d, J=10.1 Hz), 4.99-4.88 (2H, m), 3.77 (3H, s), 3.75 (1H,s), 3.64 (3H,s), 3.62 (3H, s), 2.48-3.36 (2H, m), 2.87-2.65 (5H, m), 2.68 (3H,s), 2.61-2.45 (2H, m), 2.34-2.00 (5H, m), 2.06 (3H, s), 1.83 (1H, m), 1.65-1.40 (5H, m), 1.12-1.09 (2H, m), 0.50 (3H, t, J=7.25 Hz). $^{13}$C NMR ($CDCl_3$) 175.45, 171,68, 170.63, 158.25, 152.52, 140.79, 135.44, 130.32, 127.67, 124.18, 123.34, 123.10, 121.10, 120.70, 119.88, 119.12, 110.87, 100.75, 93.96, 83.24, 79.60, 76.30, 62.05, 60.26, 55.65, 53.99, 53,16, 52.14, 52.09, 51.91, 50.66, 44.08, 42.73, 38.31, 32.71, 31.83, 30.66, 21.00, 16.35, 7.62, and four 3° carbons too weak. HRMS (FAB). Calcd for $C_{45}H_{57}N_4O_8(M^++1)$, 781.4176. Found m/e 781.4199.

(+)-18'S-4'-Desethyl-4'-deshydroxy-7',8'-bisnorvinblastine 16

The N-allyl adduct 15 (0.20 g, 0.256 mmol) in 1,2-dichloroethane (15 ml), containing proton sponge (0.060 g, 0.282 mmol), at 25° C., was treated with 1-chloroethyl chloroformate (0.056 ml, 0.512 mmol, 2.0 equiv) and the resulting solution stirred for 3 hrs. The mixture was evaporated in vacuo, and the residue dissolved in methanol and heated at reflux for 3 hrs. The methanol was evaporated and the residue dissolved in chloroform and purified by chromatography over silica gel eluting with $CHCl_3MeOH$, 10% aqueous $NH_4OH$ (20:1) to give the 18bisnorvinblastine 16 (0.155 g. 82%). M.p. 175–177° C. $[\alpha]_D^{23} = +16.25°$ (c=0.4 in $CHCl_3$). CD (MeOH) $\lambda_{max}$ ($\Delta\epsilon$) 211 (−53.3), 222 (+35.9), 256 (+17.4), 305 (+2.8), 312 (+2.8). IR ($CHCl_3$) 3448, 2932, 1740, 1616, 1502, 1457, 1434, 1373, 1235 and 1041 cm$^{-1}$. UV (MeOH) $\lambda_{max}$ ($\epsilon$) 215 (51700), 265 (15700), 310 (5480) nm. $^1$H NMR ($CDCl_3$) $\delta$9.70 (1H, s), 8.97 (1H, bs), 7.52 (1H, d, J=7.60 Hz), 7.23 (1H, d, J=7.86 Hz), 7.09 (2H, m), 6.55 (1H, s), 6.31 (1H, s), 6.05 (1H, s), 5.84 (1H, dd, J's=10.1 and 3.8 Hz), 5.41 (1H, s), 5.28 (1H, d, J=10.1 Hz), 3.78 (3H, s), 3.73 (3H, s), 3.72 (1H, s), 3.69 (3H, s), 3.35 (1H, m), 2.98 (1H, dd, J's=12.1 and 2.7 Hz), 2.88–2.75 (2H, m), 2.70 (3H, s), 2.61 (1H, s), 2.55–2.36 (3H, m), 2.24 (2H, m), 2.09 (3H, s), 2.05 (1H, d, J=4.3 Hz), 1.73 (5H, m), 1.51–1.39 (2H, m), 1.27 (1H, m), 1.27 (1H, m), 0.83 (1H, m), 0.57 (3H, t, J=7.4 Hz). $^{13}$C NMR ($CDCl_3$) $\delta$175.16, 171.54, 170.72, 158.33, 152.59, 138.73, 130.09, 127.70, 124.29, 123.09, 122.00, 121.78, 121.52, 120.13, 119.31, 110.82, 102.29, 93.63, 83.07, 79.72, 76.35, 65.45, 53.36, 52.81, 52.24, 50.51, 50.40, 46.60, 44.42, 42.59, 39.17, 38.27, 33.43, 32.51, 30.59, 26.14, 21.04, 7.91. HRMS (FAB). Calcd for $C_{42}H_{53}N_4O_8$ ($M^++1$), 741.3863 Found m/e 741.3863.

(−)-18'R-4'-Desethyl-4'-deshydroxy-7', 8'-bisnorvinblastine 18

The 18'-epimer was made as above in 75% yield. It has M.p. 203—204° C. $[\alpha]_D^{23} = -93.3°$ (c=1.55 in $CHCl_3$). CD (MeOH) $\lambda_{max}$ ($\Delta\epsilon$) 208 (−23.6), 220 (−26.3), 268 (+3.5), 305 (−1.55), 312 (−1.16U. IR ($CHCl_3$) 3436, 3000, 2942, 1737, 1614, 1501, 1454, 1434, 1372, 1240, 1040 cm$^1$. $\delta$max ($\epsilon$) 212.4 (21700), 265 (6890), 304 (2670) nm. $^1$H NMR ($CDCl_3$) $\delta$9.71 (1H, s), 7.51 (1H, d, J=7.68 Hz), 7.32 (1H, d, J=7.97 Hz), 7.08 (2H, m), 6.65 (1H, s), 10 6.27 (1H, s), 6.04 (1H, s), 5.86 (1H, dd, J's=10.0 and 3.9 Hz), 5.37 (1H, s), 5.25 (1H, d, J=10.1 Hz), 3.78 (3H, s), 3.77 (1H, s), 3.70 (3H, s), 3.67 (3H, s), 3.65–3.34 (3H, m), 2.86 (2H, d, J =15.5 Hz), 2.70 (3H, s), 2.67 (1H, s), 2.65–2.51 (3H, m), 2.31–2.02 (5H, m), 2.07 (3H, s), 1.91–1.09 (5H, m), 0.52 (3H, t, J=7.18 Hz). $^{13}$C NMR ($CDCl_3$) $\delta$175.17, 171.63, 170.72, 158.18, 152.61, 140.23, 135.53, 130.19, 127.63, 124.35, 123.41, 122.62, 121.31, 121.13, 120.05, 119.24, 110.90, 101.06, 93.71, 83.09, 79.67, 76.29, 65.57, 55.69, 53.18, 52.16, 52.06, 50.80, 50.53, 45.68, 44.00, 42.70, 42.04, 38.23, 32.68, 31.00, 30.65, 25.05, 21.01, 7.61. HRMS (FAB). Calcd for $C_{42}H_{35}N_4O_8(M^++1)$, 741.3863. Found m/e 741.3863.

EXAMPLE 2

Preparation of Dihydrodesethyl Navelbine 5

(+)-18'S-4'-Desethyl-4'-deshydroxy-7'-norvinblastine

To a solution of the (+)-norvinblastine 16 (43 mg, 0.058 mmol) in dioxane (4 ml) and glacial acetic acid (1ml) was added 37% aqueous formaldehyde (2 ml) and the mixture stirred at 35° C. for 24 hrs. The solution was evaporated in vacuo and the residue suspended in chloroform and washed with cold aqueous 5% $K_2CO_3$ solution. The chloroform layer was dried ($MgSO_4$), filtered, and evaporated. The residue was chromatographed eluting with EtOAc/MeOH, 10% $NH_4OH$ to give the dihydrodesethyl compound 5 (35 mg 81%). M.p. 195–197° C. (MeOH/$Et_2O$). $[\alpha]_D^{23}=+56.7°$ (c=1.5 $CHCl_3$). CD (MeOH) $\lambda_{max}$ ($\Delta\epsilon$) (MeOH) 209 (−18.9), 221 (+72.3), 55 (+27.7), 298 (+7.9), 309 (+7.8). IR ($CHCl_3$) 3456, 2995, 2940, 1740, 1616, 1505, 1460, 1434, 1373 and 1236 cm$^{-1}$. $\lambda_{max}$ (6) 213 (67100), 265 (20920), 310 (6870) nm. $^1$H NMR ($CHCl_3$) $\delta$9.86 (1H, s), 8.42 (1H, s), 7.75 (1H, bd, J=2.1 Hz), 7.14 (3h, m), 6.34 (1H, s), 6.08 (1H, s), 5.84 (1H, dd, J's=4.0 and 10.2 Hz), 5.40 (1H, s), 5.27 (1H, d, J=10.1 Hz), 4.66 (1H, d, J=13.0 Hz), 4.42 (1H, bs), 3.81 (3H, s), 3.78 (3H, s), 3.71 (3H, s), 2.70 (3H, s), 2.55 (1H, s), 2.10 (3H, s), 0.70 (3H, t, J=7.3 Hz). $^{13}$C NMR ($CDCl_3$) $\lambda$174.9, 171.6, 170.9, 157.9, 152.5, 134.6, 129.9, 128.9, 124.6, 123.0, 122.5, 122.4, 121.0, 119.5, 118.4, 111.5, 110.4, 93.8, 83.2, 79.7, 75.1, 65.2, 55.7, 55.5, 53.2, 52.5, 52.1, 51.0, 50.4, 50.2, 48.5, 45.9, 44.4, 42.6, 38.8, 30.9, 30.6, 29.6, 21.1, 14.1, 8.1. HRMS (FAB). Calcd for $C_{43}H_{53}N_4O_8(M^++)$, 753.3863 Found m/e 753.3878.

(+)-18'R-4'-Desethyl-4'-deshydroxy-7'-norvinblastine 19

M.p. 237° C. (dec). $[\alpha]_D^{23} = -86.7°$ (c=1.5 in $CHCl_3$). CD (MeOH) $\lambda_{max}$ ($\Delta\epsilon$) 208 (+54.7), 221.5 (−59.2), 271 (+12.9), 294 (−3.0). IR ($CHCl_3$) 3423, 3003, 2931, 1742, 1615, 1498, 1459, 1432, 1372, 1231 and 1039 cm$^1$. $\lambda_{max}$ ($\Delta\epsilon$) (MeOH) 214 (47600), 267 (14030) nm. $^1$H NMR ($CDCl_3$) $\delta$9.72 (1H, s), 9.12 (1H, s), 7.70 (1H, d, J=7.15 Hz), 7.22 (1H, d, J=7.04 HZ), 7.11 (2H, m), 6.3 (1H, s), 6.11 (1H, s), 5.86 (1H, dd, J's =10.17 and 3.67 Hz), 5.34 (1H, s), 5.25 (1H, d, J=10.18 Hz), 4.48 (1H, d, J=12.57 Hz), 4.27 (1H, d, J=12.57 Hz), 3.91 (3H, s), 3.77 (6H, bs), 3.70 (1H, s), 3.44–3.18 (3H, m), 2.88–2.53 (5H, m), 2.70 (3H, s), 2.45–2.03 (5H, m), 2.07 (3H, s), 1.89 (2H, m), 1.63 (2H, m), 1.09 (1H, m), 0.56 (3H, t, J=7.28 Hz). $^{13}$C NMR ($CDCl_3$) $\delta$174.77, 171.53, 170.78, 156.51, 152.30, 134.77, 130.16, 128.33, 125.75, 124.51, 123.97, 122.01, 120.76, 119.31, 118.39, 110.43, 94.21, 82.95, 79.68, 76.30, 65.45, 56.02, 54.16, 53.11, 52.18, 52.15, 51.52, 50.55, 50.43, 48.18, 45.35, 43.58, 42.62, 39.40, 38.30, 30.55, 21.04, 13.60, 7.58. HRMS (FAB). Calcd for $C_{43}H_{53}N_4O_8$ ($M^++1$), 753.3863. Found m/e 753.3878.

EXAMPLE 3

Synthesis of Navelbine Derivatives

The following procedures indicate the methods contemplated by the inventors for the preparation of navelbine analogs bridged at the tryptamine via a connecting atom to the number 9 carbon position on the indole ring.

Synthesis of 8'-Hydroxymethylnavelbine

α- and β-epimers of 8'-Hydroxymethylnavelbine

The parent sec-amine, 18-bis norvinblastine, is dissolved in acetic acid or other polar solvent and treated with 2-t-butyldimelthylsilyl(oxy)acetaldehyde at room temperature or, at elevated temperatures if necessary. A mixture of α- and β-t-BuMeSiOCH$_2$CH-derivatives is produced. The stereoisomers are readily separated using separation methods well known to those of skill in the art.

8'-keto-navelbine

The parent sec-amine, 18-bis norvinblastine, is dissolved in tetrahydrofuran and reacted with one equivalent of phosgene. The product ketone is then separated.

8'-aza-navelbine

The parent sec-amine, 18-bis nor vinblastine, is dissolved in acetic acid with sodium nitrite. Reduction with zinc dust produces the nitrogen bridged compound.

EXAMPLE 4
Biological Activity of (+)-18'S-4'-desethyl-4'-deshydroxy-7'-norvinblastine The 18'(S)-epimer was tested in vitro for antitumor activity in comparison with the 18'(R)-epimer and vinblastine. IC$_{50}$'s were determined in a 72 hr cytotoxicity assay. Results are shown in Table 1.

TABLE 1

| Compound | IC$_{50}$ (μg/ml) |
| --- | --- |
| Vinblastine | 0.0005 |
| 18'(S)-Dihydrodesethylnavelbine | 0.0005 |
| Navelbine | 0.005 |
| 18'(R)-Dihydrodesethylnavelbine | no activity |

REFERENCE

The references listed below are incorporated by reference to the extent they supplement, explain, provide a background for or teach methodology, techniques and/or compositions employed herein.

1. Binet, S., Chaineau, E., Fellous, A., Lataste, H., Krikorian, A., Couzinier, J.P., Meininger, V., Int. J. Cancer 46, 262–266 (1990).
2. Fellous, A., Ohayon, R., Vacassin, T., Binet, S., Lataste, H., Krikorian, A., Couzinier, J.P., and Meininger, V., Semin. Oncol. 16, 9–14 (1989).
3. Gueritte, F. Pouilhe, A., Mangeney, P. Andriamialisoa, R.O., Langlois, N., Langlois, Y. and Potier, P., Eur. J. Med. Chem.-Chim. Ther., 419–424 (1983).
4. Langlois, N., Langlois, Y., Andriamialisoa, R.Z., Potieo, P. and Mangeney, P., U.S. Patent No. 4,307,100, Dec. 22, 1981.
5. Lhomme, C., Rev. Prat. (France) 40, 1780–1781 (1990).
6. Maral, R., Bounut, C., Chenn, E. and Mathe, G., Cancer Chemother. Pharmacol. 5 (3), 197–199 (1981).
7. Potier, P. in Seminars in Oncology, John W. Yarbro, Ed., Harcourt Brace Jovanovich, Inc., 1989, Vol. 16, No. 2, Suppl. 4 (April), pp. 2–4.
8. Akkerman, A.M., de Jongh, D.K., Veldstra, H., Rec. Trav. Chim. Pays-Bas., 70, 899 (1951).
9. Bettoni, G., Duranti, E., Tortorella, V., Gazz. Chim. Ital., 102, 189 (1972).
10. Büchi, G., Manning, R.E. and Monti, S.A., J. Am. Chem. Soc. 86, 4631.

What is claimed is:

1. A process for the preparation of desethyldihydro navelbine having the formula:

comprising the steps of:

(a) condensing an amine-protected piperidinyl Grignard reagent having the formula:

where Z is an amine-protecting group and Y is lower alkyl or hydrogen;

with a N-protected 2-methoxyoxalyl indole to form an N-protected-α-hydroxyester having the formula:

where X is an N-protecting group;

(b) removing the N-protecting group X from the 2-methoxyoxalyl indole to produce an α-hydroxyester having the formula:

(c) coupling (4) with vindoline having the formula:

to produce a dimeric compound having the formula:

(d) removing the protecting group Z from the amine-protected piperidyl moiety in (6); and

(e) ring closing the deprotected piperidyl nitrogen of the dimeric compound with formaldehyde (6) to produce desethyldihydro navelbine (1).

2. A process for the preparation of desethyldihydro navelbine having the formula:

comprising the steps:

(a) reducing an R(—) ester of nipecoic acid having the formula:

wherein R is lower alkyl and Z is an amine-protecting function, to produce a primary alcohol having the formula:

(b) preparing a Grignard reagent from the primary alcohol (3) to produce a compound having the formula:

(c) condensing the Grignard reagent (4) with N-phenylsulfonyl-2-methoxyoxalyl indole to form an N-phenylsulfonyl-α-hydroxyester having the formula:

(d) cleaving the phenylsulfonyl group from (5) to produce an α-hydroxyester having the formula:

(e) coupling (6) with vindoline having the formula:

to produce a dimeric compound having the formula:

(f) removing the protecting Z group of the dimer (8); and (g) ring closing the deprotected amine group of the dimeric compound (8) with formaldehyde to produce desethyldihydro navelbine (1).

3. The process of claim 2 wherein the reducing step (a) is with lithium aluminum chloride.

4. The process of claim 1 or claim 2 wherein the amine protecting function Z is selected from a group consisting of allyl, benzyl and carbobenzyloxy.

5. The process of claim 2 wherein the cleaving step (d) is a reductive cleavage.

6. The process of claim 5 wherein the reductive cleavage is with sodium naphthalenide in dimethoxyethane at low temperatures.

7. The process of claim 6 wherein the low temperature is between about −40° and −70° C.

8. The process of claim 6 wherein the reductive cleavage is followed by quenching with trifluoroacetic acid.

9. The process of claim 1 wherein the ring closing is an intramolecular Mannich reaction with formaldehyde.

* * * * *